(12) United States Patent
Brannick et al.

(10) Patent No.: US 11,235,126 B2
(45) Date of Patent: Feb. 1, 2022

(54) REINFORCED SHEATH FOR A STEERABLE SHEATH ASSEMBLY

(71) Applicant: Baylis Medical Company Inc., Montreal (CA)

(72) Inventors: Ros Thomas Brannick, East York (CA); Brian Ma, Toronto (CA); Audrey Chan, Richmond Hill (CA); Melanie Thompson Smith, Toronto (CA); Bei Ning (Alice) Zhang, Pasadena, CA (US); Neil Godara, Milton (CA); Jan-Hung Chen, Georgetown (CA); Michael Froncioni, St-Lazare (CA); David Mulligan, Leitrim (IE)

(73) Assignee: Baylis Medical Company Inc., Mississauga (CA)

( * ) Notice: Subject to any disclaimer, the term of this patent is extended or adjusted under 35 U.S.C. 154(b) by 0 days.

(21) Appl. No.: 16/753,979

(22) PCT Filed: Oct. 5, 2018

(86) PCT No.: PCT/IB2018/057765
§ 371 (c)(1),
(2) Date: Apr. 6, 2020

(87) PCT Pub. No.: WO2019/069291
PCT Pub. Date: Apr. 11, 2019

(65) Prior Publication Data
US 2021/0001088 A1    Jan. 7, 2021

Related U.S. Application Data

(60) Provisional application No. 62/569,346, filed on Oct. 6, 2017.

(51) Int. Cl.
*A61M 25/01*    (2006.01)

(52) U.S. Cl.
CPC .... *A61M 25/0147* (2013.01); *A61M 25/0105* (2013.01)

(58) Field of Classification Search
CPC ..................... A61M 25/0147; A61M 25/0105
See application file for complete search history.

(56) References Cited

U.S. PATENT DOCUMENTS

| 2003/0135156 A1* | 7/2003 | Bencini ............ A61M 25/0144 |
| | | 604/95.04 |
| 2010/0168827 A1 | 7/2010 | Schultz |
| | (Continued) | |

FOREIGN PATENT DOCUMENTS

WO    2016175882 A    11/2016

OTHER PUBLICATIONS

Patent Corporation Treaty, International Search Report for PCT Application No. PCT/IB2018/057765, dated Apr. 9, 2019.

(Continued)

*Primary Examiner* — Rebecca E Eisenberg
*Assistant Examiner* — John A Doubrava
(74) *Attorney, Agent, or Firm* — Vincent Man; Glenn Arnold; Samuel Tekie

(57) ABSTRACT

A method and apparatus are disclosed for a reinforced steerable sheath assembly that is usable with an actuator comprising a shaft section defining a sheath that is operable to be deflected, and one or more pull wires that are coupled to the sheath via a coupling at a point of contact between the pull wires and the sheath. The pull wires being operable to be coupled to the actuator for actuating the pull wires. The reinforced steerable sheath assembly further comprises a means for preventing displacement of the coupling, wherein the means for preventing displacement to minimize failure at (Continued)

the coupling at the point of contact between the pull wires and the sheath upon actuation of the pull wires upon actuation of the actuator to deflect the sheath.

13 Claims, 8 Drawing Sheets

(56) References Cited

U.S. PATENT DOCUMENTS

| | | |
|---|---|---|
| 2012/0123332 A1 | 5/2012 | Christian |
| 2012/0123337 A1 | 5/2012 | Miller |
| 2013/0281925 A1* | 10/2013 | Benscoter ......... A61M 25/0147 604/95.04 |
| 2014/0336572 A1* | 11/2014 | Heisel .................... A61L 29/06 604/95.04 |
| 2017/0136213 A1 | 5/2017 | Kauphusman et al. |

OTHER PUBLICATIONS

Patent Corporation Treaty, Written Opinion for PCT Application No. PCT/IB2018/057765, dated Apr. 9, 2019.

* cited by examiner

--Prior Art--

--Prior Art--

REINFORCED SHEATH FOR A STEERABLE SHEATH ASSEMBLY

TECHNICAL FIELD

The disclosure relates to a reinforced sheath for a steerable sheath assembly. More specifically, the present disclosure relates to a steerable sheath assembly that provides a reinforced sheath at the point of contact of the pull wires to the sheath.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
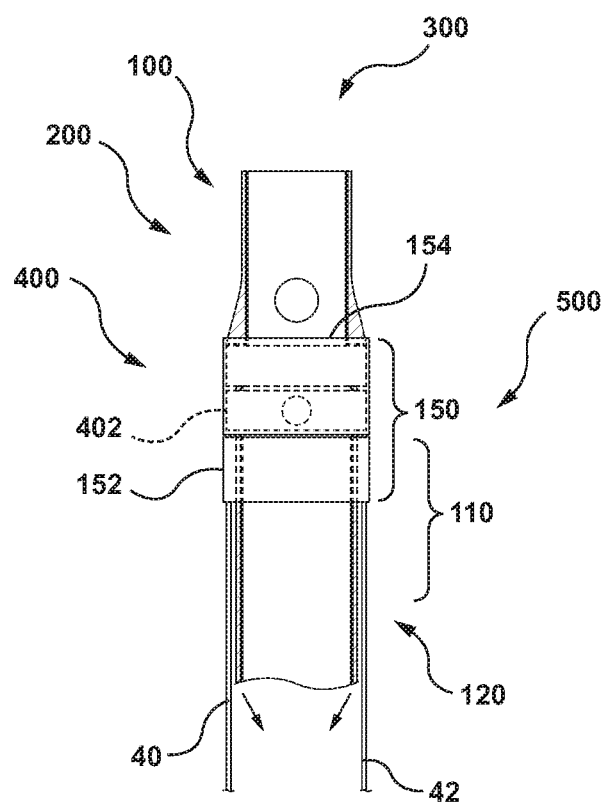
FIG. 1A-1F are an illustration of a steerable sheath assembly in accordance with various embodiments of the present invention.

Some medical procedures may require the use of a steerable sheath or catheter in order to reach a desired location within a patient's body in order to treat the patient. The steerable sheath or catheter may be deflectable upon actuation of a steerable sheath or catheter control handle. Some such steerable catheter control handles comprise actuation mechanisms that are actuable to deflect the sheath by actuating of one or more control or pull wires that are coupled to the sheath. In some such examples, the one or more pull wires may be coupled to the sheath along a distal segment of the sheath, allowing the actuator to deflect a distal portion of the sheath at the desired curvature.

However, some such steerable sheaths may not be able to withstand a high degree of deflection of the sheath, and/or repeated actuation of the sheath without failure. In some such examples, high degree of deflection of the steerable sheath and/or repeated deflections of the steerable sheath may result in failure of the steerable sheath at the point of contact of the pull wires with the sheath. Furthermore, such sheaths may not be able to perform adequately without failure when one or more devices are used in conjunction with the steerable sheath and the steerable sheath is used to curve the assembly. In some such examples, the steerable sheath may be used with a needle and/or a dilator positioned within the steerable sheath, and the steerable sheath may be curved. Some such prior art systems may observe failure at the pull wire connection at the sheath, due to the stress or strain put on the sheath from curving the one or more rigid devices along with it due to higher forces and greater actuation required to deflect the sheath.

The inventors of the present invention have discovered a unique problem associated with prior art steerable sheath assemblies that result in failure at the point of contact between the pull wires and the sheath and presented a novel solution to solve the same. The present inventors have discovered that in prior systems the failure at the point of contact between the pull wires and the sheath is a result of the weakness in the portion of the shaft of the sheath where the pull wires are connected.

In some embodiments of systems that use pull rings to connect the pull wires to the sheath, the present inventors have discovered that there is weakness in the segment of the shaft at the point/interface where the pull wires are connected to the sheath, via the pull ring. The present inventors have additionally discovered that the weakness may result in displacement and or pivoting of the pull-wire out of position about the point of attachment of the pull ring to the sheath such as the pull-ring anchor hole, upon deflection of the steerable sheath. As such the weakness in the shaft may result in displacement of the coupling between the pull wires and the shaft. In some cases the pull ring may be able to pivot or displace proximally behind a deflectable section of the sheath that may be immediately proximal to the coupling [such as a pull ring]. In some such situations, as the pull wires are deflected, the angle between the pull wire and the coupling [such as pull-ring] may become greater than 90 degrees due to weakness in the shaft resulting in curvature at the joint between the pull-wires and the pull-ring which may be a weld-joint, which may result in breaking of the weld-joint due to breakage.

In some embodiments, the coupling [such as a pull-ring] may be able to pivot at the pull-ring anchor hole which is a hole through which the polymer layers of shaft of the sheath through flow to form a peg to keep the pull-ring in place, once the pull wires are deflected, resulting in rotational displacement of the pull-ring.

As will be presently described, the present inventors have additionally discovered a unique solution to solving the problem by providing a means for preventing displacement of the coupling. The present inventors have discovered and invented embodiments for reinforcing the area of the shaft of the steerable sheath where the pull wires are coupled, to help minimize failure at the interface between the pull wires and sheath.

In systems where a pull ring is used to couple one or more pull wires to the shaft of the steerable sheath, present inventors have discovered unique solutions to reinforce an area of the steerable sheath shaft where the pull ring is located.

In one broad aspect, embodiments of the present invention comprise a reinforced steerable sheath assembly that is usable with an actuator comprising: a shaft section defining a sheath that is operable to be deflected, and one or more pull wires that are coupled to the sheath via a coupling at a point of contact between the pull wires and the sheath. The pull wires are operable to be coupled to the actuator for actuating the pull wires. The reinforced steerable sheath assembly further comprises a means for preventing displacement of the coupling, wherein the means for preventing displacement to minimize failure at the coupling at the point of contact between the pull wires and the sheath upon actuation of the pull wires upon actuation of the actuator to deflect the sheath.

As a feature of this broad aspect, the means for preventing displacement of the coupling comprises a reinforcement/reinforced section for reinforcing the coupling, wherein the reinforcement, defines a portion of the sheath.

As example of this feature, the reinforcement/reinforced section is defined by/comprises a proximal reinforcement/reinforced section that is positioned behind the coupling to prevent displacement of the coupling upon actuation of the pull wires.

As a further example of this feature, the reinforcement/reinforced section is defined by/comprises an encapsulating reinforcement/reinforced section that is positioned around/over the coupling to help prevent proximal displacement and rotational displacement of the coupling.

In one instance of this example, the encapsulating reinforcement/reinforced section is formed integrally with the proximal reinforcement/reinforced section.

In some embodiments of the present invention, the reinforcement/reinforced section enables an angle between the pull wire and the coupling to be maintained substantially at about 90 degrees during actuation.

As an example of this feature, the reinforcement/reinforced section is defined by/comprises an encapsulating reinforcement/reinforced section that is positioned around/over the coupling to help prevent proximal displacement and rotational displacement of the coupling.

As an example of any one of the examples described herein above, the coupling comprises a pull-ring.

In one such example, the reinforcement/reinforced section is defined by/comprises at least two pull ring anchor holes for coupling the pull ring to the sheath.

In another example, the reinforcement/reinforced section comprises an integrated pull-ring that is coupled to one or more components of the sheath to minimize displacement by providing a longer fulcrum requiring greater force to displace the pull-ring.

In a specific instance of this example, the integrated pull-ring comprises a pull-ring that is coupled to a marker band.

As another example of this feature, the reinforcement comprises at least two connections/points of contact for connecting the coupling to the sheath.

As still another example of this feature, the reinforcement/reinforced section comprises an integrated coupling that is connected to one or more components of the sheath to minimize displacement by providing a longer fulcrum requiring greater force to displace the coupling.

In one such example, the integrated coupling comprises a coupling that is connected to a marker band.

As still another example of this feature, the reinforcement/reinforced section comprises a polymer under layer, to enable the coupling to be captured substantially between the polymer under layer and a polymer over layer defining a portion of the shaft to be surrounded thereby.

In a further broad aspect, embodiments of the present invention comprise a reinforced steerable sheath assembly that is usable with an actuator comprising, a shaft section defining a sheath that is operable to be deflected, and one or more pull wires that are coupled to the sheath via a coupling at a point of contact between the pull wires and the sheath. The pull wires being operable to be coupled to the actuator for actuating the pull wires. The reinforced steerable sheath assembly further comprises a reinforcement/reinforced section for reinforcing the coupling, the reinforcement/reinforced section defining a portion of the sheath, wherein the reinforcement/reinforced section prevents displacement of the coupling to help minimize failure at the coupling upon actuation of the actuator to actuate the pull wires to deflect the sheath.

In a further broad aspect, embodiments of the present invention comprise a reinforced steerable sheath assembly that is usable with an actuator comprising, a shaft section defining a sheath that is operable to be deflected. The shaft section has a proximal end and a distal end and the actuator is positioned proximate the proximal end of the shaft section. The reinforced steerable sheath assembly further comprises a coupling attached proximate the distal end of the shaft section, and one or more pull wires. A distal end of the pull wires are coupled proximate the distal end of the shaft section via the coupling, and the proximal end of the pull wires being coupled to the actuator for actuating the pull wires. The reinforced steerable sheath assembly further comprises a means for preventing displacement of the coupling positioned proximate to the coupling, whereby said means helps to minimize failure of the coupling at a point of contact between the pull wires and the coupling, and at a point of contact between the coupling and the sheath, upon actuation of the pull wires to deflect the sheath.

As a feature to this broad aspect, the means for preventing displacement of the coupling comprises a reinforced section for reinforcing the coupling.

As example of this feature, the reinforced section comprises a proximal reinforcement member positioned proximal to the coupling to prevent displacement of the coupling upon actuation of the pull wires.

In one such example, the reinforcement member supports the coupling to prevent displacement.

As a further example of this feature, the reinforced section comprises an encapsulating member that is positioned over the coupling to prevent proximal displacement and rotational displacement of the coupling upon actuation of the pull wires.

In one such example, the reinforced section further comprises a proximal reinforcement member positioned proximal to the coupling.

As a further example of the feature, the the encapsulating member is integral with the proximal reinforcement member.

As an example of any one of the examples described herein above, the coupling comprises a pull-ring.

As example of this feature, the reinforced section comprises at least two pull ring anchor holes for coupling the pull ring to the shaft section.

Another example of this feature, the reinforced section comprises an integrated pull-ring that is coupled to one or more components of the sheath to minimize displacement by providing a longer fulcrum requiring greater force to displace the pull-ring.

In a specific instance, the integrated pull-ring comprises the pull-ring coupled to a marker band.

As a feature to this broad aspect, the reinforced section comprises at least two points of contact for connecting the coupling to the shaft section.

As another feature to the broad aspect, the reinforced section comprises an integrated coupling that is connected to one or more components of the sheath to minimize displacement by providing a longer fulcrum requiring greater force to displace the coupling.

As a further example of this feature, the integrated coupling comprises the coupling connected to a marker band.

As another feature of the broad aspect, the reinforced section comprises a polymer under layer, to enable the coupling to be captured substantially between the polymer under layer and a polymer over layer defining a portion of the shaft to be surrounded thereby.

As an example of any one of the examples described herein above, the reinforced steerable sheath further comprising a locking member, wherein the at least one pull wire is attached at the distal end of the at least one pull wire to the locking member. The locking member is dimensioned to fixably couple to a corresponding aperture on the coupling, whereby when the locking member and aperture are coupled, the pull wires are fixed relative to the coupling.

In a specific instance, the locking member comprises a rectangular member and the aperture is a rectangular slot.

As an example of any one of the examples described herein above, the reinforced section is a substantially rigid polymer.

In a specific instance, the substantially rigid polymer comprises 72D Pebax or Nylon 12.

In some embodiment of the present invention, the reinforced section substantially maintains an angle between the pull wire and the coupling to be about 90 degrees during actuation.

In some embodiment of the present invention, the section substantially proximal to the coupling is straight.

In a further broad aspect, a reinforced steerable sheath assembly comprising, a shaft section defining a sheath that is operable to be deflected, the shaft section having a proximal end and a distal end, and an actuator positioned proximate the proximal end of the shaft section. The reinforced steerable sheath assembly further comprises a coupling attached proximate the distal end of the shaft section, and one or more pull wires. A distal end of the pull wires are coupled proximate the distal end of the shaft section via the coupling and wherein a proximal end of the pull wires are coupled to the actuator. The steerable sheath assembly further comprises a reinforced section positioned proximate to the coupling, wherein the reinforced section prevents displacement of the coupling upon actuation of the pull wires to deflect the sheath.

With specific reference now to the drawings in detail, it is stressed that the particulars shown are by way of example and for purposes of illustrative discussion of certain embodiments of the present invention only.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. In one embodiment of the present invention, as shown in FIG. 1A, a reinforced steerable sheath assembly 300 is provided that is usable with an actuator. The reinforced steerable sheath assembly 300 comprises a shaft section 100 that defines a sheath 200 that is operable to be deflected. The reinforced steerable sheath assembly 300 further comprises one or more pull wires 40, 42 that are coupled to the sheath 100 via a coupling 400 at a point of contact between the pull wires 40, 42 and the sheath 200.

The pull wires 40, 42 are operable to be coupled to an actuator for actuating the pull wires 40, 42. The reinforced steerable sheath assembly 300 additionally comprises a means 500 for preventing displacement of the coupling 400. In some such embodiments, the means 500 for preventing displacement of the coupling comprises a reinforcement/reinforced section 150 for reinforcing the coupling 400 [for example by reinforcing an area of the shaft 100 around the coupling 400], wherein the reinforcement/reinforced section 150 defines a portion of the sheath 200. In the example shown, the means 500 for preventing displacement (a reinforcement/reinforced section 150) helps to minimize failure at the coupling 400 at the point of contact between the pull wires 40, 42 and the sheath 200 (or in other words a portion of the shaft 100 of the sheath 200) upon actuation of the pull wires upon actuation of the actuator to deflect the sheath.

Figure 1B:
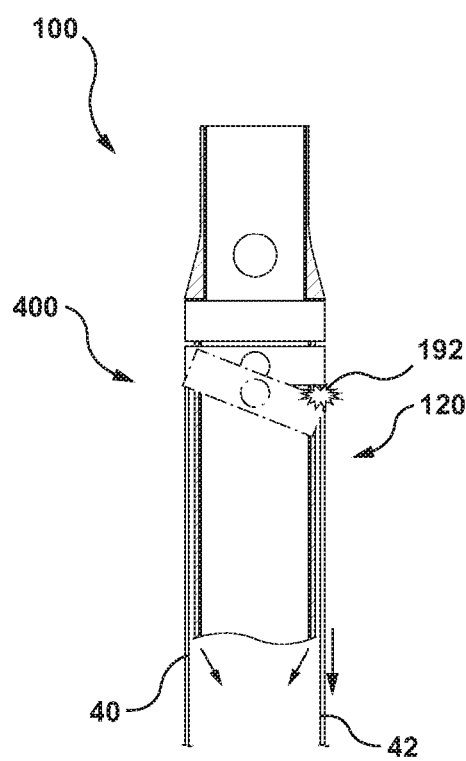
Figure 1C:
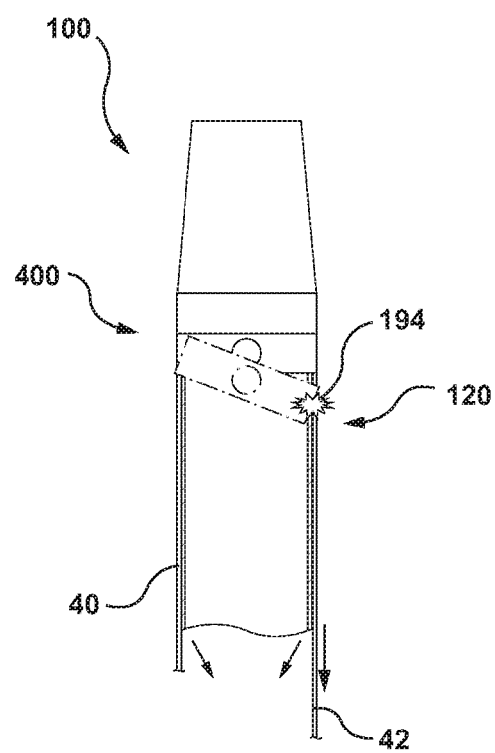

In accordance with the embodiment as shown in FIG. 1A, the means for preventing displacement of the coupling, such as a reinforcement/reinforced section 150 prevents both proximal displacement of the coupling 400 [such as a pull-ring 402] as well as rotational displacement or pivoting of the coupling [such as the pull-ring 402]. The proximal displacement and rotational displacement or pivoting is shown with respect to FIGS. 1B and 1C showing embodiments of sheath assemblies, for illustrative purposes only. Proximal displacement occurs when the coupling 400 displaces proximally towards the proximal end of the shaft, and in some cases, the displaced coupling interferes with or is positioned proximally to the deflectable section of the sheath 120. This typically results from failure of the means for attaching the coupling 400 to the shaft, which is illustrated at item 192 in FIG. 1B. Rotational displacement occurs when the coupling 400 pivots and experiences rotational displacement around an axis (for example, where the coupling 400 is fixed using a single anchor point, coupling 400 rotationally displaces about the axis created by that anchor point) and the angle between the coupling 400 and the pull wire 40, 42 is no longer maintained at 90 degrees. The curvature at the joint between the coupling 400 and the pull wire 40, 42 may result in breaking of the joint as illustrated at item 194 in FIG. 1C. Failure may result from a combination of both rotational and proximal displacement.

Reinforcement/Reinforced Section

Proximal Reinforcement/Reinforced Section and Encapsulating Reinforcement/Reinforced Section In some embodiments of the present invention, the reinforcement/reinforced section enables the angle between the pull wire and the coupling 400 to be maintained substantially at about 90 degrees during actuation.

Figure 1D:
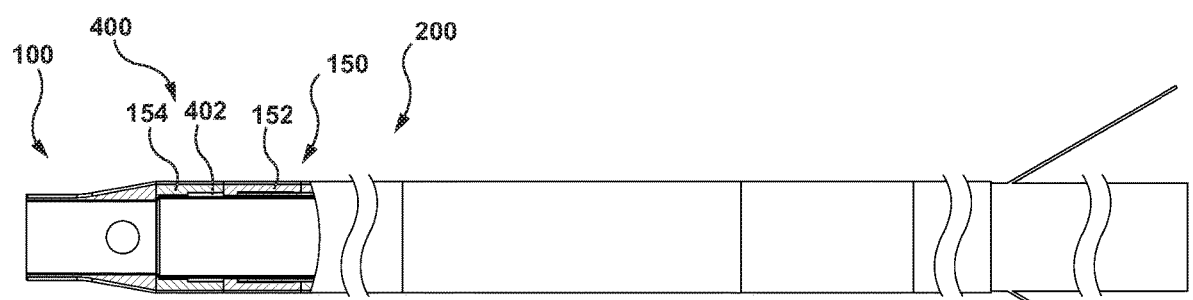
Figure 1F:
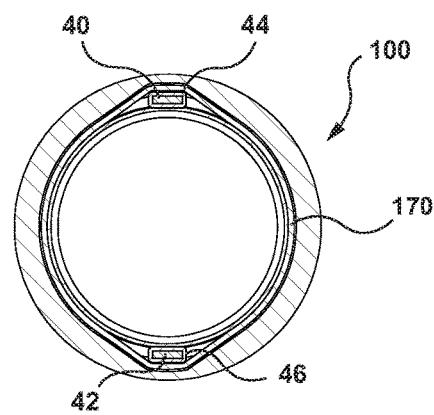
Figure 1E:
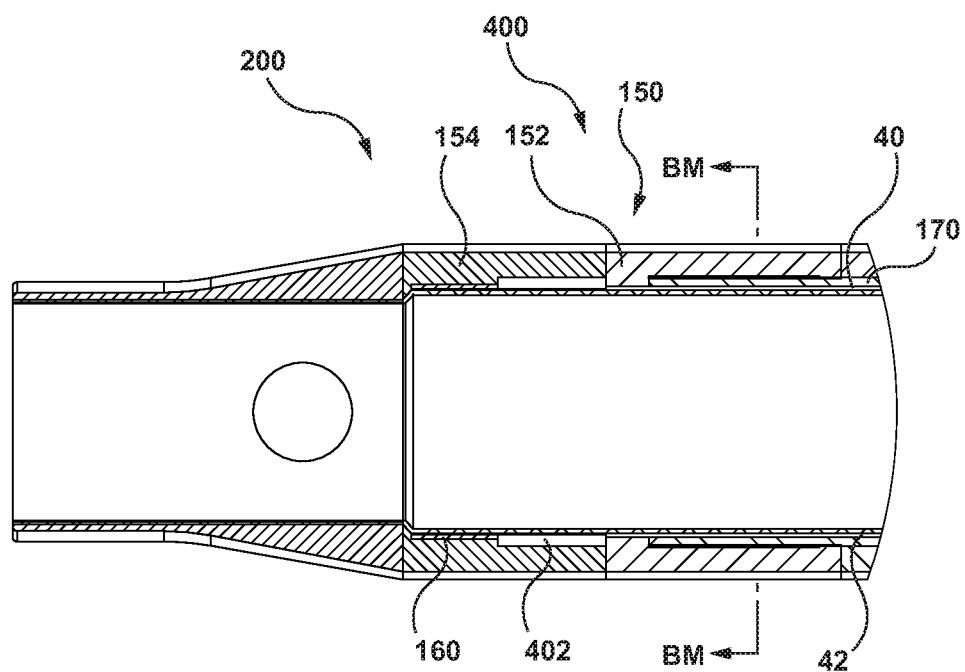

With reference again to FIG. 1A as well in FIGS. 1D and 1E, in one embodiment of the present invention, the reinforcement/reinforced section 150 is defined by/comprises a proximal reinforcement member such as proximal reinforcement/reinforced section 152 that is positioned behind the coupling 400 [such as the pull ring 402] to prevent displacement of the coupling 400 upon actuation of the pull wires 40, 42. The proximal reinforcing/reinforced section 152 in some examples comprises a substantially rigid section, for example comprising polymer, such as portion of Nylon 12. In some such examples, of steerable sheath assembly of the present invention, the coupling 400 is positioned distal to the bendable or deflectable portion of the shaft, which in some examples comprises a 35D durometer section of Pebax polymer. As such, the proximal reinforcing/reinforced section 152 functions as a stop to prevent rotation of the coupling 400 [such as pull-ring 402], and additionally can help prevent the coupling 400 [such as pull-ring 402], from slipping proximally and/or behind the deflectable section 120 of the sheath 200 [which is now proximal to the reinforcing/reinforced section 152]. In some examples the proximal reinforcement/reinforced or reinforcing section 152 may also capture a distal end of a braid of the shaft 100 to capture the frayed edges therein. FIG. 1F is a cross section of the specific embodiment of a reinforced sheath 200 seen in FIG. 1E along the cut-line BM. The specific embodiment has two pull wire lumens 44, 46 secured under layer 170 (e.g., a braided wire). The pull wires 40, 42 run through the pull wire lumens 44, 46 along the length of the shaft 100.

In some embodiments of the present invention, with reference again to FIGS. 1A, 1D and 1E, the reinforcement/ reinforced section 150 is defined by or comprises an encapsulating member such as an encapsulating reinforcement/reinforced section 154 that is positioned around/over the coupling 400 [such as pull-rings 402] to help prevent proximal displacement and rotational displacement of the coupling. The reinforcement/reinforced section 154 functions to cap and/or grip the coupling 400 [such as pull-rings 402] to substantially minimize the movement or displacement of the pull-ring under deflection of the pull-wires. In some such embodiments, the encapsulating reinforcement/reinforced section 150 additionally encapsulates a marker band 160 that is positioned distal to the pull-ring 402.

In some such examples, both encapsulating reinforcement/reinforced section 154 and the proximal reinforcement/reinforced section 152 together help to encapsulate the coupling 400 [such as pull-ring 402] and keep it straight to mitigate against failure at the pull wire/pull-ring interface. The reinforcement at the joint which may be a weld joint may help prevent fatigue. In the embodiment, described herein, the proximal and encapsulating reinforcements/reinforcement sections 152, 154 may comprise a substantially rigid polymer. In some such examples, the substantially rigid polymer comprises a 72D Pebax. In other examples, the substantially rigid polymer comprises Nylon 12.

In a specific example the encapsulating reinforcement/reinforced section 154 is formed integrally with the proximal reinforcement/reinforced section 152. In some such examples, both encapsulating and proximal reinforcement/reinforced sections 154, 152 comprise Nylon 12.

In some such embodiments, encapsulating reinforcement/reinforced section 154 provided overtop the coupling 400 [such as pull-ring 402] functions grip the pull-ring 402 to prevent movement thereof and the proximal reinforcement/reinforced section 152 that is the section that is behind the pull ring 402 stops the movement of the pull-ring 402 because of stiffness of the material the defines the proximal reinforcement/reinforced section 152 such as Nylon 12.

As the pull wires are actuated, the proximal reinforcement/reinforced section 152 behind the pull-ring 402 remains substantially straight as the sheath 200 bends. Both the encapsulating reinforcement/reinforced section 154 and proximal reinforcement/reinforced section 152, keep the coupling 400 [such as pull-wire 402] substantially straight such that the angle the pull ring 402 sees (i.e. the angle between the pull-ring 402 and the pull wires 40, 42) is substantially maintained at 90 degrees. As such, the one or more pull wires 40, 42 stay at a 90 degree position to the pull ring 402. By helping to keep the pull-ring 402 straight the reinforced section 150 of the sheath (as defined by Both the encapsulating reinforcement/reinforced section 154 and proximal reinforcement/reinforced section 152) help mitigate against failure at the pull wire 40, 42/pull-ring 402 interface or joint (such as a weld-joint) and may help prevent fatigue. As the sheath 200 is deflected, the section of the shaft 100 of the sheath 200 substantially behind or proximal to weld point it is straight, and does not become part of curve.

As the shaft 110 immediately proximal to the coupling 400 [pull-ring 402] stays substantially rigid or stiff, keeping the shaft section [and thus the pull wire 40, 42] substantially straight, substantially maintaining the 90 degree angle between the pull-wires 40, 42 and the pull-ring 402.

In some embodiments, encapsulating reinforcement/reinforced section 154 overtop the pull ring 402, help to prevent it from displacing, and the straight section that is defined by the encapsulating reinforcement/reinforced section 154 (such as nylon 12 section) helps to maintain the angle at the joint between the pull ring 402 and the pull wire 40, 42 by keeping the shaft section 110 immediately proximal to the pull-ring 402 straight so that the pull wires 40, 42 can remain straight along that section maintaining an angle of about 90 degrees between the pull wire 40, 42 and the pull-ring 402. The proximal and encapsulating reinforcements/reinforcing sections 152, 154 also help displacement of the pull-ring either rotational displacement or proximal displacement.

The reinforced steerable sheath, where the reinforcement/reinforced section enables an angle between the pull wire and the coupling to be maintained substantially at about 90 degrees during actuation.

Alternate Embodiments of
Reinforcement/Reinforced Section

Reinforcement Under Layer

In some embodiments of the present invention, the steerable sheath assembly may be provided with a reinforcement/reinforced section that comprises one or more of the alternative reinforcement/reinforced section as provided in the present disclosure.

Figure 2A:
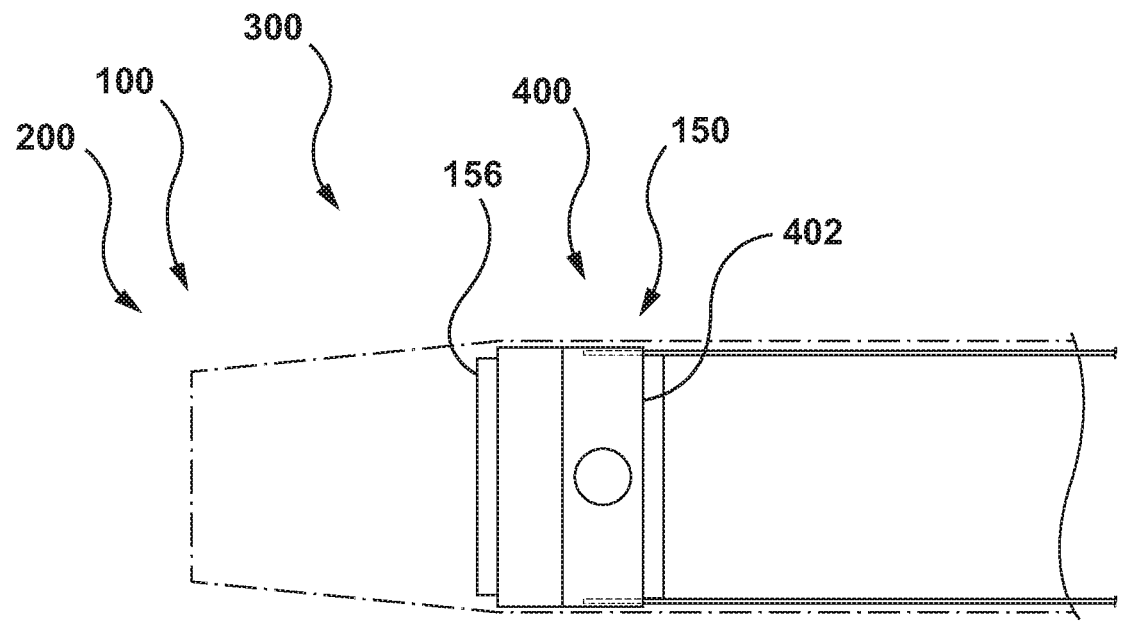
FIGS. 2A-2D are an illustration of a steerable sheath assembly in accordance with various alternate embodiments of the present invention.

In an alternate embodiment of the present invention, as shown in FIG. 2A, a reinforcement/reinforced section 150 is provided that is defined by/comprises a reinforcement under layer 156 that is provided under the pull-ring 402. Under layer 156 may be a polymer under layer to enable the coupling 400 [such as pull-ring 402] to be captured substantially between the reinforcement under layer 156 and a polymer over layer, and as such the pull-ring 402 is encapsulated and supported by the surrounding structures. In some instances the section of the shaft over the pull-ring is the encapsulating reinforcement/reinforced section 154, as additionally shown in FIG. 2D. In some such embodiments, the pull-ring 402 is embedded or captured and supported within the polymer layers of the shaft at the coupling. As shown in FIG. 2D, the encapsulating reinforcement/reinforced section 154 increases the stiffness of the outer layer over the rings. In some such examples, the encapsulating reinforcement/reinforced section 154 comprises 72D Pebax layer. In other examples the reinforced section 154 comprises Nylon 12.

Figure 2B:
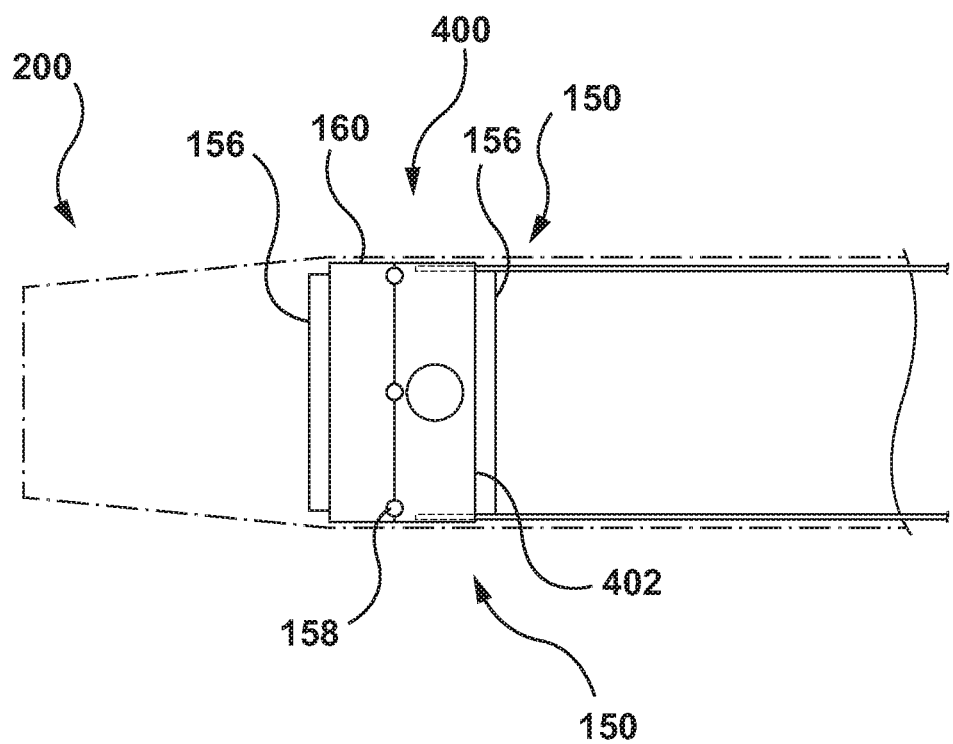

In an alternate embodiment of the present invention, as shown in FIG. 2B, a reinforced steerable sheath 200 is provided. In this embodiment, the reinforcement/reinforced section 150 comprises an integrated coupling 158 where the coupling 400 [such as pull-ring 402] is connected to one or more components of the sheath 200 to minimize displacement of the coupling 400 [such as pull-ring 402]. In some embodiments, the integrated coupling 158 results in a longer fulcrum (relative to a coupling 400 alone) by lengthening the area of contact between the sheath and the coupling 400/integrated coupling 158. By providing a longer fulcrum, greater force is required to displace the coupling 400 as more support is provided by the layers of the sheath. In one particular example, the pull ring 402 is welded to the marker band 160 as shown in FIG. 2B. In some examples, the pull ring 402 may be welded to the marker band 160 along one or more points to form one or more welds. As such in some instances, the integrated coupling 158 comprises a coupling 400 that is connected to a marker band 160.

In some embodiments, the dimensions of the coupling 400 may be modified to achieve a longer fulcrum. For example, the body of the coupling 400 may be lengthened resulting in a greater area of contact between coupling 400 and layers of the sheath.

Figure 2C:
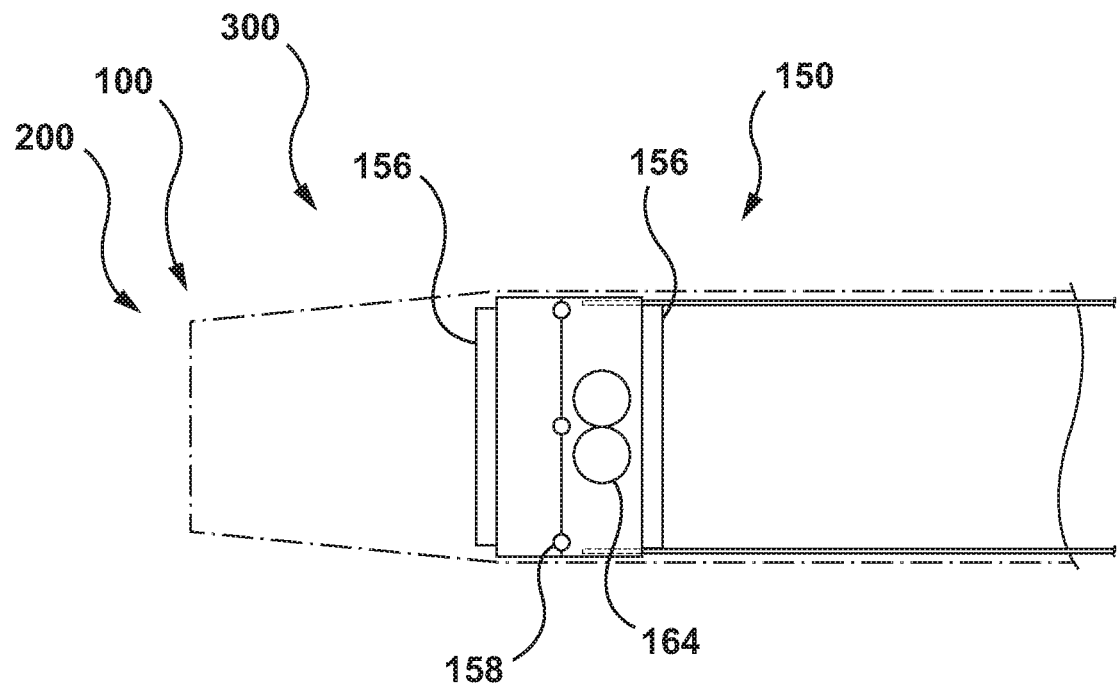
Figure 2D:
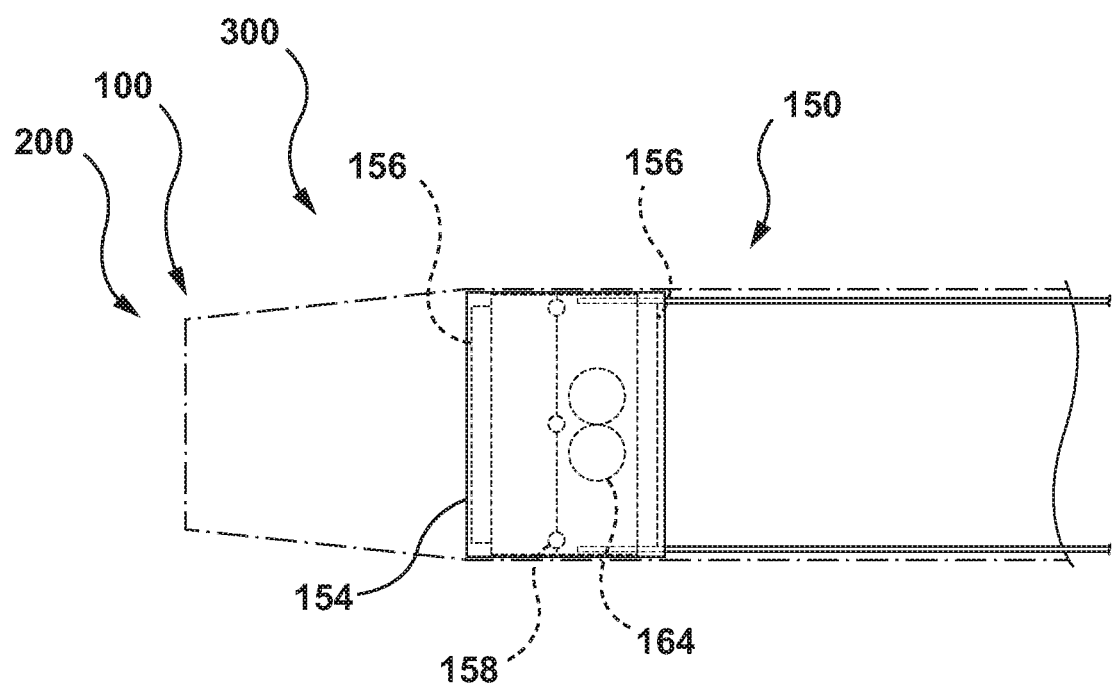

Multiple Connections/Points of Contact for Connecting the Coupling to the Sheath In alternate embodiments of the present invention, a reinforced steerable sheath 200 is provided as shown in FIG. 2C, wherein the reinforcement/reinforced section 150 comprises at least two connections/points of contact for connecting the coupling 400 [such as pull-ring] to the sheath. In one specific example, the at least two connections/points of contact are at least two pull ring anchor holes 164 for coupling the pull ring to the sheath. Once the pull ring 402 is coupled to a section of the shaft 100 of the sheath 200, the polymer around the pull ring flows through the pull ring anchor holes 164 to form pegs. In some such instances, the pull ring anchor holes 164 (and thus pegs) may be spaced apart from the midpoint between the pull-wires. In some such examples, the pull ring anchor holes 164 (and thus pegs) are positioned so that they are not too close to the pull wires so they do not see too much pulling from the pull-wires. Alternate exemplary embodiments of pull-ring anchor hole patterns can be seen in FIGS. 3A and 3B. By providing more than one pull ring anchor hole and (thus more than one peg), more than one anchoring point is provided between the coupling and the pull ring 402 which may prevent rotation of the pull-ring. By additionally spacing the pegs, the pivoting may be reduced as any force experienced by the pull ring is applied at two or more points instead of one. Spacing the more than one pull ring anchor holes (and thus more than one pegs) additionally distributes the points at which force is applied. Thus, the rotational force is distributed to multiple parts of the pull ring.

In some such embodiments, the plurality of holes prevent rotation about a point and are provided towards the periphery to minimize rotation. In one example two holes that are provided that are off centered but are not be in line with pull wires. The holes may be one or two smaller holes vs a larger hole. The smaller holes may be provided further away from the wires and may be less inclined to impact the integrity of the weld between the pull wires and the pull ring.

Figure 3A:
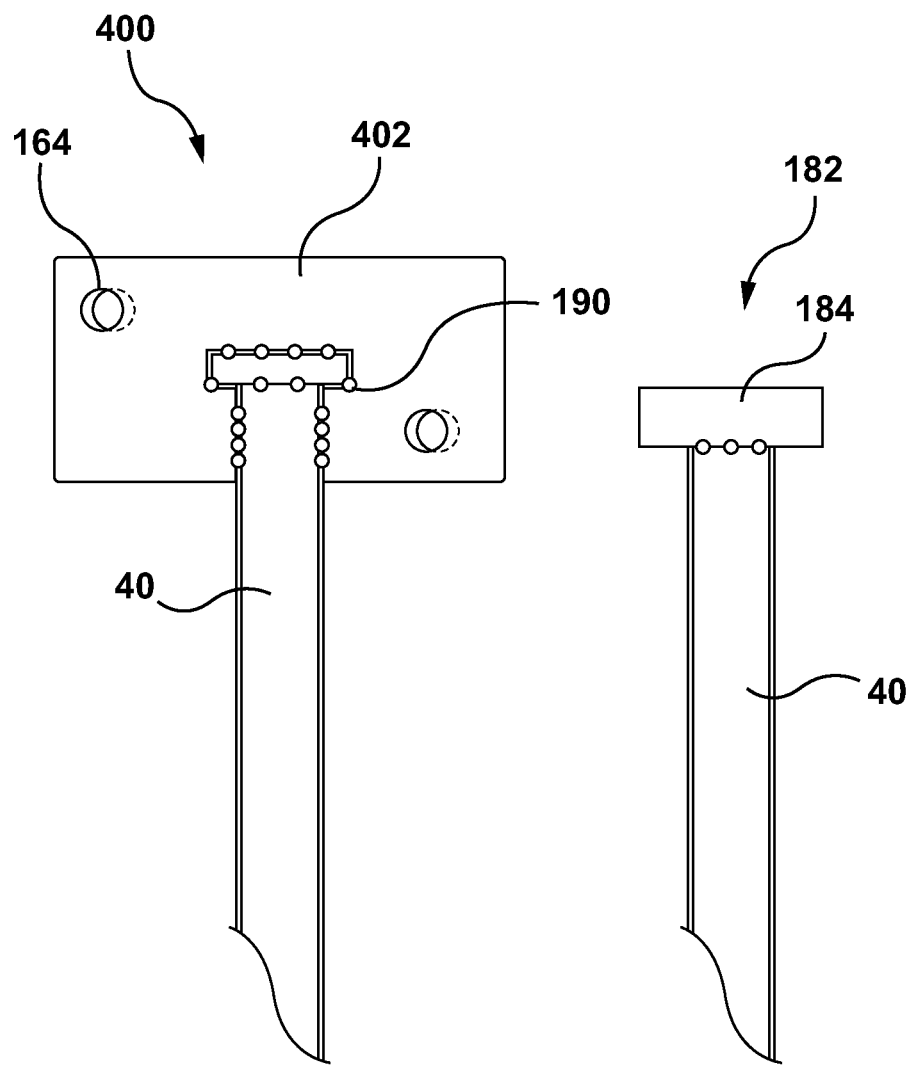
FIG. 3A is an illustration of a pull-ring/pull wire assembly with a mechanical lock.
Figure 3B:
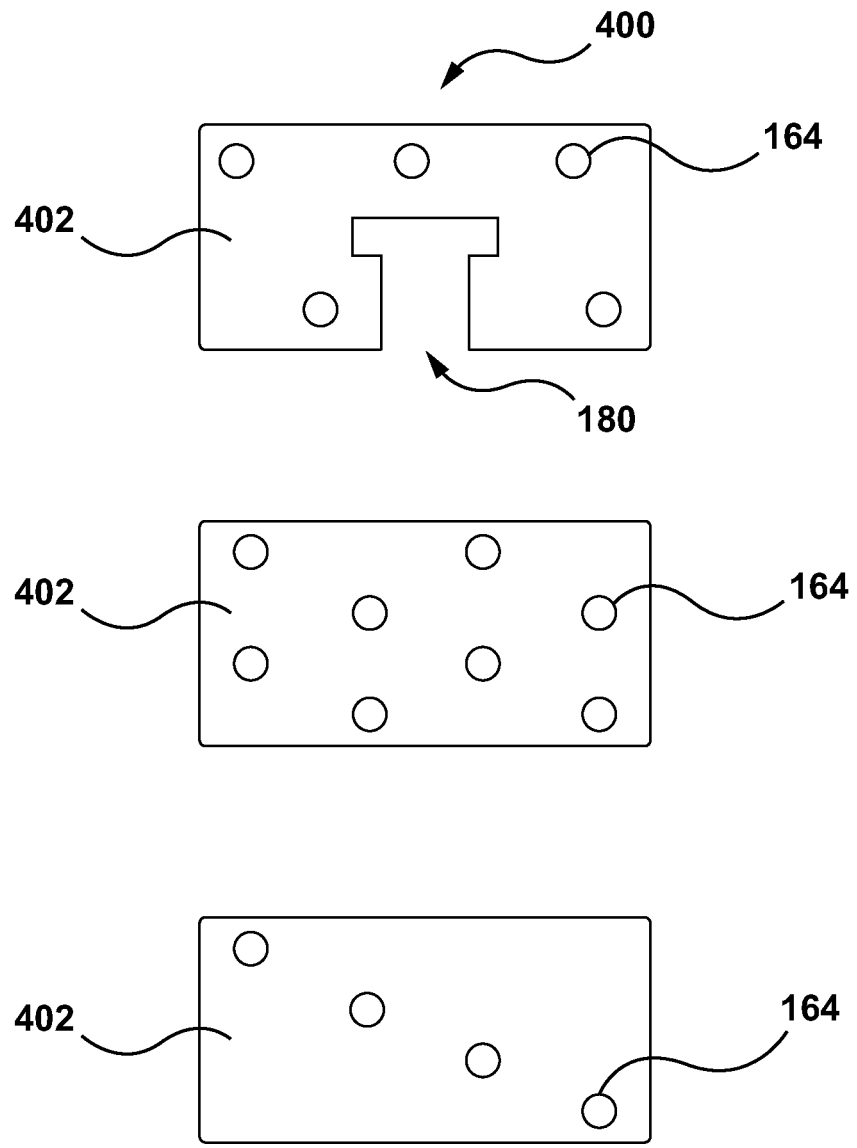
FIG. 3B is an illustration of multiple anchor holes on a pull-ring.

In an alternate embodiment of the present invention, a coupling 400 (such as a pull-ring 402) is provided as seen in FIGS. 3A and 3B, wherein the coupling 400 comprises a slot 180 for receiving a locking member 182. Locking member 182 may be integral with pull wires 40, 42 or may be attached thereto. Welding or other attachment means (adhesives, etc.) may be used to attach the pull wires 40, 42 to the locking member 182. In one example, the pull-ring 402 has a slot 180 between the pull-ring 402 and pull wires 40, 42. By attaching the pull wires 40, 42 to the pull ring 402 using the slot 180 and locking member 182, force which is applied to the pull wires 40, 42 may be distributed throughout the engagement surfaces between the locking member 182 and slot 180. This in turn reduces the likelihood that the joint between the pull-ring 402 and the pull wires 40, 42 will break. In the embodiment depicted in FIGS. 3A and 3B, the locking member 182 is a rectangular member 184 which is attached to pull wires 40, 42 via a series of attachment points using various attachment means (such as welds 190). Pull ring 402 comprises a slot 180 which has a corresponding shape adapted to receive the locking member 182. Those skilled in the art will appreciate that slots and locking members of varying dimensions may be used. During assembly, slot 180 of the pull ring 402 receives the locking member 182 and attachment means are used to secure the locking member 182 to the pull ring 402. Various attachment means are known in the art, such as welding, adhesives, and fasteners.

Further Examples

1. A reinforced steerable sheath assembly that is usable with an actuator comprising:
   a shaft section defining a sheath that is operable to be deflected;
   one or more pull wires that are coupled to the sheath via a coupling at a point of contact between the pull wires and the sheath;
   the pull wires being operable to be coupled to the actuator for actuating the pull wires; and
   a means for preventing displacement of the coupling; wherein the means for preventing displacement helps to minimize failure at the coupling at the point of contact between the pull wires and the sheath upon actuation of the pull wires upon actuation of the actuator to deflect the sheath.
2. The reinforced steerable sheath of example 1, wherein the means for preventing displacement of the coupling comprises a reinforcement/reinforced section for reinforcing the coupling, wherein the reinforcement, defines a portion of the sheath.
3. The reinforced steerable sheath of example 1, wherein the reinforcement/reinforced section is defined by/comprises a proximal reinforcement/reinforced section that is positioned behind the coupling to prevent displacement of the coupling upon actuation of the pull wires.
4. The reinforced steerable sheath of example 1, wherein the reinforcement/reinforced section is defined by/comprises an encapsulating reinforcement/reinforced section that is positioned around/over the coupling to help prevent proximal displacement and rotational displacement of the coupling.
5. The reinforced steerable sheath of example 2, wherein the reinforcement/reinforced section is defined by/comprises an encapsulating reinforcement/reinforced section that is positioned around/over the coupling to help prevent proximal displacement and rotational displacement of the coupling.
6. The reinforced steerable sheath of example 5, wherein encapsulating reinforcement/reinforced section is formed integrally with the proximal reinforcement/reinforced section.
7. The reinforced steerable sheath of any one of example 1 to 6, where the reinforcement/reinforced section enables an angle between the pull wire and the coupling to be maintained substantially at about 90 degrees during actuation.
8. The reinforced steerable sheath of any one of example 1 to 6, wherein the coupling comprises a pull-ring.
9. The reinforced steerable sheath of example 8, wherein the reinforcement/reinforced section is defined by/comprises at least two pull ring anchor holes for coupling the pull ring to the sheath.
10. The reinforced steerable sheath of example 8, wherein the reinforcement/reinforced section comprises an integrated pull-ring that is coupled to one or more components of the sheath to minimize displacement by providing a longer fulcrum requiring greater force to displace the pull-ring.
11. The reinforced steerable sheath of example 10, wherein the integrated pull-ring comprises a pull-ring that is coupled to a marker band.
12. The reinforced steerable sheath of example 2, wherein the reinforcement/reinforced section comprises at least two connections/points of contact for connecting the coupling to the sheath.

13. The reinforced steerable sheath of example 2, wherein the reinforcement/reinforced section comprises an integrated coupling that is connected to one or more components of the sheath to minimize displacement by providing a longer fulcrum requiring greater force to displace the coupling.

14. The reinforced steerable sheath of example 13, wherein the integrated coupling comprises a coupling that is connected to a marker band.

15. The reinforced steerable sheath of example 2, wherein the reinforcement/reinforced section comprises a polymer under layer, to enable the coupling to be captured substantially between the polymer under layer and a polymer over layer defining a portion of the shaft to be surrounded thereby.

16. A reinforced steerable sheath assembly that is usable with an actuator comprising:
 a shaft section defining a sheath that is operable to be deflected;
 one or more pull wires that are coupled to the sheath via a coupling at a point of contact between the pull wires and the sheath;
 the pull wires being operable to be coupled to the actuator for actuating the pull wires; and
 a reinforcement/reinforced section for reinforcing the coupling, the reinforcement/reinforcement section defining a portion of the sheath;
 wherein the reinforcement/reinforced section prevents displacement of the coupling to help minimize failure at the coupling upon actuation of the actuator to actuate the pull wires to deflect the sheath.

In one broad aspect, embodiments of the present invention comprise a reinforced steerable sheath assembly that is usable with an actuator comprising: a shaft section defining a sheath that is operable to be deflected, and one or more pull wires that are coupled to the sheath via a coupling at a point of contact between the pull wires and the sheath. The pull wires are operable to be coupled to the actuator for actuating the pull wires. The reinforced steerable sheath assembly further comprises a means for preventing displacement of the coupling, wherein the means for preventing displacement to minimize failure at the coupling at the point of contact between the pull wires and the sheath upon actuation of the pull wires upon actuation of the actuator to deflect the sheath.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A reinforced steerable sheath assembly comprising:
 a shaft section defining a sheath that is operable to be deflected, the shaft section having a proximal end and a distal end, an actuator being positioned proximate the proximal end of the shaft section; and
 a reinforced section that defines a portion of the distal end of the shaft section, the reinforced section further comprising:
 a coupling attached proximate the distal end of the shaft section;
 one or more pull wires, wherein a distal end of the one or more pull wires are coupled proximate the distal end of the shaft section via the coupling, a proximal end of the one or more pull wires being coupled to the actuator for actuating the one or more pull wires;
 a polymer under layer that is positioned under the coupling;
 a polymer over layer that is positioned over the coupling, wherein the polymer under layer and the polymer over layer enable the coupling to be encapsulated to prevent proximal displacement and rotational displacement of the coupling upon actuation of the one or more pull wires, whereby the polymer under layer and the polymer over layer do not form a portion of the to the shaft section proximal reinforced section; and
 a proximal reinforcement member positioned proximal to the coupling to further prevent displacement of the coupling upon actuation of the one or more pull wires;
 whereby the reinforced section reinforces the coupling and helps to minimize failure of the coupling at a point of contact between the one or more pull wires and the coupling, and at a point of contact between the coupling and the sheath, upon actuation of the one or more pull wires to deflect the sheath.

2. The reinforced steerable sheath assembly of claim 1 wherein the proximal reinforcement member comprises a rigid polymer that functions as a stop to prevent rotation or movement of the coupling upon actuation of the one or more pull wires.

3. The reinforced steerable sheath assembly of claim 1, wherein the polymer over layer is formed integrally with the proximal reinforcement member.

4. The reinforced steerable sheath assembly of claim 1, wherein the reinforced section substantially maintains an angle between the one or more pull wire and the coupling to be about 90 degrees during actuation.

5. The reinforced steerable sheath assembly of claim 1, wherein the coupling comprises a pull ring.

6. The reinforced steerable sheath assembly of claim 1, wherein the reinforced section comprises an integrated pull ring that is coupled to one or more components of the sheath to minimize displacement by providing a longer fulcrum to lengthen an area of contact between the sheath and the integrated pull ring.

7. The reinforced steerable sheath assembly of claim 1, wherein the reinforced section comprises at least two points of contact for connecting the coupling to the shaft section.

8. The reinforced steerable sheath assembly of claim 1, wherein the reinforced section comprises an integrated coupling that is connected to one or more components of the sheath to minimize displacement by providing a longer fulcrum to lengthen an area of contact between the sheath and the integrated coupling.

9. The reinforced steerable sheath assembly of claim 1, wherein the reinforced section further comprises a locking member, wherein the distal end of the one or more pull wires is attached to the locking member, and wherein the locking member is dimensioned to fixably couple to a corresponding aperture on the coupling, whereby when the locking member and the corresponding aperture are coupled, the at least one pull wire is fixed relative to the coupling.

10. The reinforced steerable sheath assembly of claim 1, wherein a proximal portion of the reinforced section captures a distal end of a braided under layer of the shaft section to capture frayed edges therein.

11. The reinforced steerable sheath assembly of claim 5, wherein the pull ring comprises at least two pull ring anchor holes for coupling the pull ring to the shaft section.

12. The reinforced steerable sheath assembly of claim 6, wherein the integrated pull ring comprises a pull ring coupled to a marker band.

13. The reinforced steerable sheath assembly of claim 8, wherein the integrated coupling comprises a coupling connected to a marker band.

\* \* \* \* \*